US007115786B2

(12) United States Patent
Khachik

(10) Patent No.: US 7,115,786 B2
(45) Date of Patent: Oct. 3, 2006

(54) METHOD FOR PRODUCTION OF β-CRYPTOXANTHIN AND α-CRYPTOXANTHIN FROM COMMERCIALLY AVAILABLE LUTEIN

(75) Inventor: Frederick Khachik, Rockville, MD (US)

(73) Assignee: University of Maryland, College Park, College Park, MD (US)

( * ) Notice: Subject to any disclaimer, the term of this patent is extended or adjusted under 35 U.S.C. 154(b) by 0 days.

(21) Appl. No.: 10/503,498

(22) PCT Filed: Feb. 6, 2003

(86) PCT No.: PCT/US03/03440

§ 371 (c)(1),
(2), (4) Date: Aug. 5, 2004

(87) PCT Pub. No.: WO03/066547

PCT Pub. Date: Aug. 14, 2003

(65) Prior Publication Data
US 2005/0119506 A1  Jun. 2, 2005

Related U.S. Application Data

(60) Provisional application No. 60/354,249, filed on Feb. 6, 2002.

(51) Int. Cl.
*C07C 35/21* (2006.01)
*C07C 35/18* (2006.01)
*C07C 41/00* (2006.01)
(52) U.S. Cl. .................. 568/816; 568/825; 568/668
(58) Field of Classification Search ............... 568/816, 568/825, 668
See application file for complete search history.

(56) References Cited

U.S. PATENT DOCUMENTS

| 4,235,820 | A  |   | 11/1980 | Evans |         |
|-----------|----|---|---------|-------|---------|
| 6,420,614 | B1 | * | 7/2002  | Eugster et al. | 568/816 |
| 6,818,798 | B1 | * | 11/2004 | Khachik | 568/816 |
| 6,911,564 | B1 | * | 6/2005  | Khachik | 568/816 |

FOREIGN PATENT DOCUMENTS

| GB | 1081104      | 8/1967  |
|----|--------------|---------|
| GB | 1427690 A    | 3/1976  |
| WO | WO 99/20587 A1 | 4/1999 |
| WO | WO 01/83414 A1 | 11/2001 |
| WO | WO 02/10128 A2 | 2/2002 |

OTHER PUBLICATIONS

Aidhen, I.S., and Narasimhan, N.S., "A novel and versatile synthesis of 1-arylbenzocyclobutenols and 1-arylbenzocyclobutenes," *Ind. J. Chem.* 32B:234-238, Council of Scientific & Industrial Research (1993).

Buchecker, R., et al., "Absolute Konfiguration von Xanthophyll (Lutein)," *Helv. Chim. Acta* 57:631-656, Schweizerische Chemische Gesellschaft (1974).

Buchecker, R. et al., CAPLUS Abstract, Accession No. 1974:437671 (1974).

da S. Costa, J. et al., "Deoxygenation of Furanmethanols with $ZnI_2$-$NaCNBH_3$. An Efficient Protocol for the Preparation of 2- and 3-alkylfuran Compounds," *J. Braz. Chem. Soc.* 5:113-116, Sociedade Brasileira de Quimica (1994).

Dehmlow, E.V., et al., "Mild and Fast Deoxygenation of Aromatic Carbonyl Compounds by Dimethylamine Borane/Titanium Tetrachloride," *Synth. Commun.* 26:1467-1472, Marcel Dekker, Inc. (1996).

Goodfellow, D., et al., "The Absolute Configuration of Lutein," *J. Chem. Soc. Chem. Commun.* 13:1578, The Chemical Society (1978).

Isler, O., et al., "Synthesen in der Carotinoid-Reihe. Totalsynthese von Kryptoxanthin und eine weitere Synthese von Zeaxanthin," *Helv. Chim. Acta.* 40:456-467 Schweizerische Chemische Gesellschaft (1957).

Isler, O. et al., CAPLUS Abstract, Accession No. 1957:62225 (1957).

Khachik, F., et al., "Isolation, structural elucidation, and partial synthesis of lutein dehydration products in extracts from human plasma," *J. Chrom. B. Biomed. Appl.* 670:219-233, Elsevier Science B.V. (1995).

Lau, C.K., et al., "Reductive Deoxygenation of Aryl Aldehydes and Ketones and Benzylic, Allylic, and Tertiary Alcohols by $ZnI_2$-$NaCNBH_3$," *J. Org. Chem.* 51:3038-3043, American Chemical Society (1986).

Loeber, D.E., et al., "Carotenoids and Related Compounds. Part XXVIII. Synthesis of Zeaxanthin, β-Cryptoxanthin, and Zeinoxanthin (α-Cryptoxanthin)," *J. Chem. Soc. (C) Part I*:404-408, The Chemical Society (1971).

Wustrow, D.J., et al., "Selective Deoxygenation of Allylic Alcohols and Acetates by Lithium Perchlorate Promoted Triethylsilane Reduction," *Tetrahedron Lett.* 35:61-64, Pergamon Press Ltd. (1994).

Zechmeister, L., and Sease, J.W., "Conversion of Lutein in a Boric Acid-Naphthalene Melt. I," *J. Am. Chem. Soc.* 65:1951-1955, American Chemical Society (1943).

International Search Report for International Application No. PCT/US03/03440, 2 pages, United States Patent and Trademark Office, Alexandria, Virginia (mailed Jul. 30, 2003).

Supplementary European Search Report for European Application No. 03713367.5, mailed Mar. 31, 2006.

* cited by examiner

*Primary Examiner*—Sikarl A. Witherspoon
(74) *Attorney, Agent, or Firm*—Sterne, Kessler, Goldstein & Fox P.L.L.C.

(57) ABSTRACT

The present invention relates to a method of reacting (3R, 3'R,6'R)-lutein with a catalytic amount of an acid to obtain a mixture of anhydroluteins, rich in anhydrolutein III, with substantially no Z-isomers being formed. The mixture is converted to (3R)-β-cryptoxanthin (major product) and (3R, 6'R)-α-cryptoxanthin (minor product) by reacting the anhydroluteins with borane-amine complexes (e.g. $Me_3N.BH_3$) or other hydride donors and an acid in a chlorinated solvent, preferably dichloromethane, at ambient temperature to produce (3R)-β-cryptoxanthin and (3R,6'R)-α-cryptoxanthin.

36 Claims, No Drawings

METHOD FOR PRODUCTION OF β-CRYPTOXANTHIN AND α-CRYPTOXANTHIN FROM COMMERCIALLY AVAILABLE LUTEIN

BACKGROUND OF THE INVENTION

1. Field of the Invention

The invention is in the field of organic chemistry. The invention relates to an efficient process for transforming commercially available (3R,3'R,6'R)-lutein containing 5–7% (3R,3'R)-zeaxanthin to anhydroluteins (dehydration products of lutein) in an alcohol at elevated temperatures and subsequent conversion of the latter to (3R)-β-cryptoxanthin as the major product and (3R,6'R)-α-cryptoxanthin as the minor product.

2. Related Art

A process for converting commercially available (3R,3'R,6'R)-lutein to a mixture of (3R,6'R)-α-cryptoxanthin, (3R)-β-cryptoxanthin, and (3R,6'R)-anhydrolutein I ((3R,6'R)-3',4'-didehydro-β,γ-caroten-3-ol), (3R,6'R)-2',3-anhydrolutein II ((3R,6'R)-2',3'-didehydro-β,ε-caroten-3-ol), and (3R)-3',4'-anhydrolutein III ((3R)-3',4'-didehydro-β,β-caroten-3-ol) in one synthetic step by allylic deoxygenation with a strong acid and a hydride ion donor was described by Khachik in U.S. patent application No. 60/220,995. The chemical structures of these carotenoids are shown in Scheme 1.

Khachik also described a two-step alternative process. The first step converted (3R,3'R,6'R)-lutein to a mixture of anhydroluteins I, II, III at room temperature with an acid. In the second step, the isolated anhydroluteins were converted to (3R,6'R)-α-cryptoxanthin and (3R)-β-cryptoxanthin with a strong acid and a hydride ion donor.

As described by Khachik, the acid-catalyzed dehydration of (3R,3'R,6'R)-lutein in a homogenous phase in a variety of solvents such as ethers (tetrahydrofuiran, tert-butyl methyl ether), chlorinated solvents (dichloromethane, chloroform, 1,2-dichloroethane), acetone, and toluene at ambient temperature leads to the formation of considerable amount of Z(cis)-isomers of anhydroluteins. In addition, under the conditions disclosed in '995 application, anhydrolutein I is the major product and anhydroluteins II and III are the minor products. Because anhydrolutein III is the precursor to (3R)-β-cryptoxanthin in the ionic hydrogenation step, a higher concentration of this carotenoid relative to anhydroluteins I and II is preferred. Therefore a modified procedure for the dehydration of (3R,3'R,6'R)-lutein is needed that can produce anhydrolutein III as the major product and at the same time significantly reduce E/Z(trans/cis)-isomerization of anhydroluteins. Such a procedure must also demonstrate that a mixture of anhydroluteins with high concentration of anhydrolutein III can be transformed into a mixture of all-E-cryptoxanthins with a high concentration of all-E-(3R)-β-cryptoxanthin. Since (3R)-β-cryptoxanthin is a precursor of vitamin A, a higher concentration of this carotenoid in the final product is desirable.

SCHEME 1

The chemical structures of (3R,3'R,6'R)-lutein, (3R,3'R)-zeaxanthin, anhydroluteins I, II, III, (3R,6'R)-α-cryptoxanthin, and (3R)-β-cryptoxanthin. The trivial and the correct systematic names for carotenoids are shown below their structures.

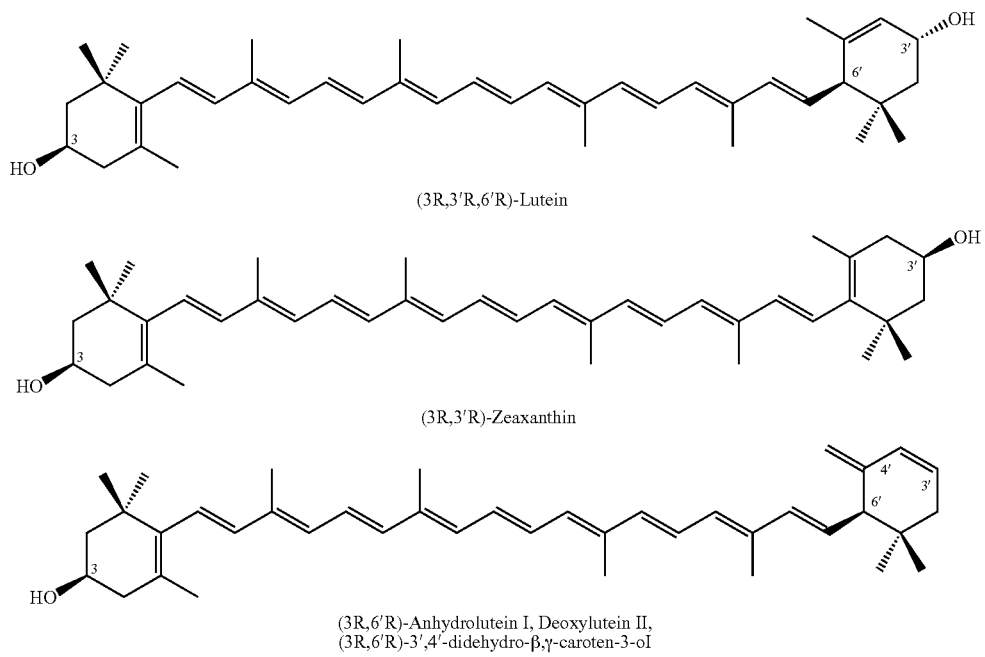

(3R,3'R,6'R)-Lutein (3R,3'R)-Zeaxanthin (3R,6'R)-Anhydrolutein I, Deoxylutein II, (3R,6'R)-3',4'-didehydro-β,γ-caroten-3-ol

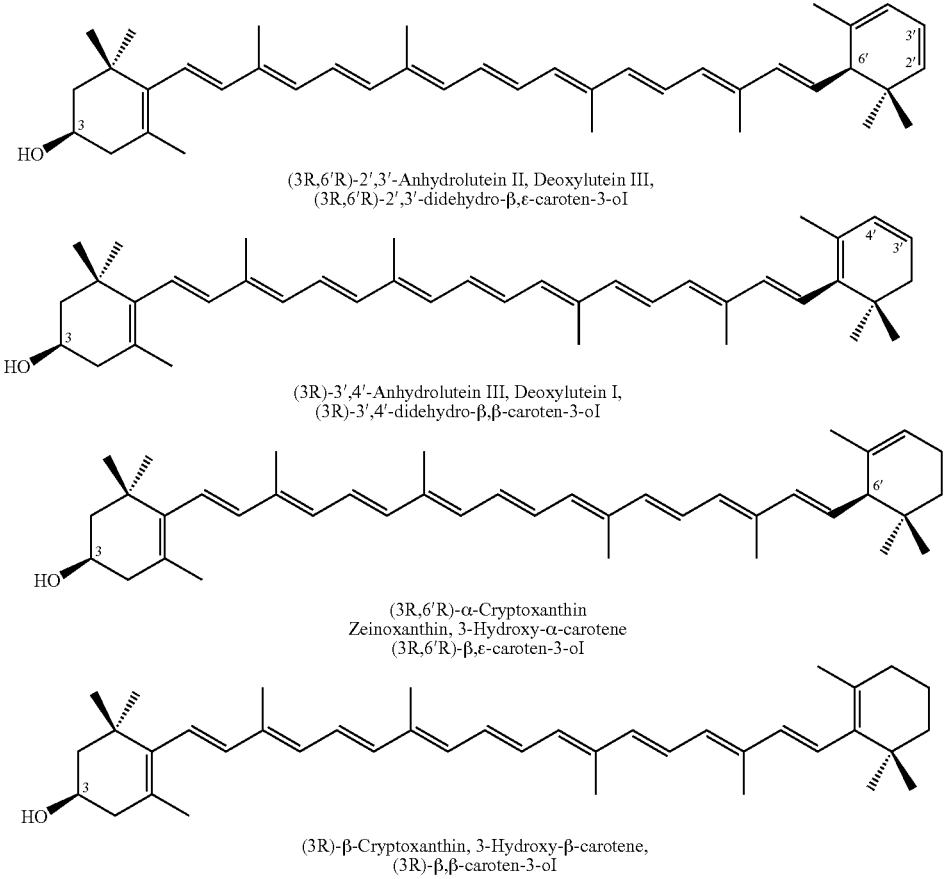

(3R,6'R)-2',3'-Anhydrolutein II, Deoxylutein III,
(3R,6'R)-2',3'-didehydro-β,ε-caroten-3-ol (3R)-3',4'-Anhydrolutein III, Deoxylutein I,
(3R)-3',4'-didehydro-β,β-caroten-3-ol (3R,6'R)-α-Cryptoxanthin
Zeinoxanthin, 3-Hydroxy-α-carotene
(3R,6'R)-β,ε-caroten-3-ol (3R)-β-Cryptoxanthin, 3-Hydroxy-β-carotene,
(3R)-β,β-caroten-3-ol

SUMMARY OF THE INVENTION

To substantially increase the yield of (3R)-β-cryptoxanthin relative to (3R,6'R)-α-cryptoxanthin in the final product and at the same time prevent any significant E/Z(trans/cis)-isomerization of the resulting carotenoids, (3R,3'R,6'R)-lutein is first dehydrated in the presence of catalytic amounts of an acid (e.g. sulfuric acid, hydrochloric acid) in an alcohol (e.g. ethanol, 1-propanol, 2-propanol, 1-butanol, 2-butanol, isobutyl alcohol, tert-butyl alcohol, 1-pentanol (n-amyl alcohol), 2-pentanol, n-hexyl alcohol, n-octyl alcohol, ethylene glycol, propylene glycol) at 78–87° C. to give a mixture of anhydrolutein I as major product and anhydroluteins II and III as minor products. As heating is continued anhydrolutein I gradually undergoes isomerization at 78–87° C. to anhydrolutein III. However, during this process considerable amount of Z(cis)-isomers of anhydroluteins are formed. To revert the Z(cis)-isomers of anhydroluteins to all-E(trans)-isomers, water is added and heating at 78–87° C. is continued until the product comprises substantially all-E-isomers of anhydroluteins. Anhydrolutein III serves as a precursor to (3R)-β-cryptoxanthin in the ionic hydrogenation step.

In an alternative process, (3R,3'R,6'R)-lutein is allowed to react with an alcohol, used as solvent, in the presence of catalytic amount of an acid between 45–50° C. to give the corresponding 3'-alkyl ethers of lutein (Scheme 2). Because the temperature is maintained below 50° C., lutein 3'-alkyl ethers do not undergo acid-catalyzed elimination to give anhydroluteins and at the same time E(trans)/Z(cis)-isomerization is also suppressed. Water and additional acid is then added to the mixture and the temperature is raised to 78–87° C. to convert the lutein 3'-alkyl ethers to a mixture of anhydroluteins I, II, and III, quantitatively. At the beginning of this transformation, once again anhydrolutein I is the major product and anhydrolutein II and III are the minor products. As heating continues at 78–87° C., anhydroluteins I and II are partially isomerized to anhydrolutein III within 7–20 h depending on the nature of the alcohol (Scheme 2).

Anhydroluteins prepared by both methods may be simply removed by filtration and then subjected to ionic hydrogenation with or without purification. In this step, the dehydration products of (3R,3'R,6'R)-lutein, comprising anhydrolutein III as the major product, are treated with a strong acid and a hydride ion donor to produce a mixture of all-E(trans)- and Z-isomers of (3R)-β-cryptoxanthin (major product) and (3R,6'R)-α-cryptoxanthin (minor product) in excellent yields. Using the same strategy described in preparation of all-E(trans)-anhydroluteins, the mixture of (E/Z)-cryptoxanthins is heated in an alcohol at 78–87° C. to revert the Z(cis)-isomers of (3R)-β-cryptoxanthin and (3R,6'R)-α-cryptoxanthin to their all-E(trans) compounds. The products formed according to this procedure do not contain any significant E/Z(trans/cis)-isomers and more than 90% of anhydroluteins are converted to all-E-(3R)-β-cryptoxanthin and all-E-α-cryptoxanthin.

In a preferred embodiment, the present invention relates to a process for converting (a) (3R,3'R,6'R)-lutein (85% total carotenoids) or (b) purified lutein (97% total carotenoids)

containing 5–7% (3R,3'R)-zeaxanthin or mixtures of (a) and (b) to a mixture of anhydroluteins I, II, and III at elevated temperature, comprising reacting (3R,3'R,6'R)-Autein in an alcohol or mixture of alcohols with a catalytic amount of an aqueous mineral acid or a strong organic acid at an elevated temperature to give a mixture of anhydroluteins comprising anhydrolutein I as the major product, anhydroluteins II and III as the minor products, and the recovered (3R,3'R)-zeaxanthin. According to this process, it is possible to obtain a mixture of anhydroluteins comprising at least 80% anhydrolutein III and substantially no Z-anhydrolutein III.

In an alternative embodiment, the present invention relates to a process for converting (a) (3R,3'R,6'R)-lutein (85% total carotenoids) or (b) purified lutein (97% total carotenoids) containing 5–7% (3R,3'R)-zeaxanthin or mixtures of (a) and (b) to lutein 3'-alkyl ether, comprising reacting (3R,3'R,6'R)-lutein with an alcohol in the presence of a catalytic amount of an aqueous mineral acid or a strong organic acid at an elevated temperature to give all-E(trans)-lutein 3'-alkyl ether and the recovered (3R,3'R)-zeaxanthin.

In an alternative embodiment, the present invention relates to A process for converting a mixture of all-E-anhydroluteins rich in all-E-anhydrolutein III, to a mixture of all-E-(3R)-β-cryptoxanthin and all-E-(3R,6'R)-α-cryptoxanthin, comprising reacting anhydroluteins containing 3–8% (3R,3'R)-zeaxanthin in a chlorinated solvent with about 1.3 equivalent of a hydride donor and about 3.5–4 equivalent of a strong organic acid at ambient temperature for about 1–5 hours to give a mixture of E/Z-(3R)-β-cryptoxanthin, E/Z-(3R,6'R)-α-cryptoxanthin, unreacted E/Z-anhydroluteins, and recovered E/Z-(3R,3'R)-zeaxanthin.

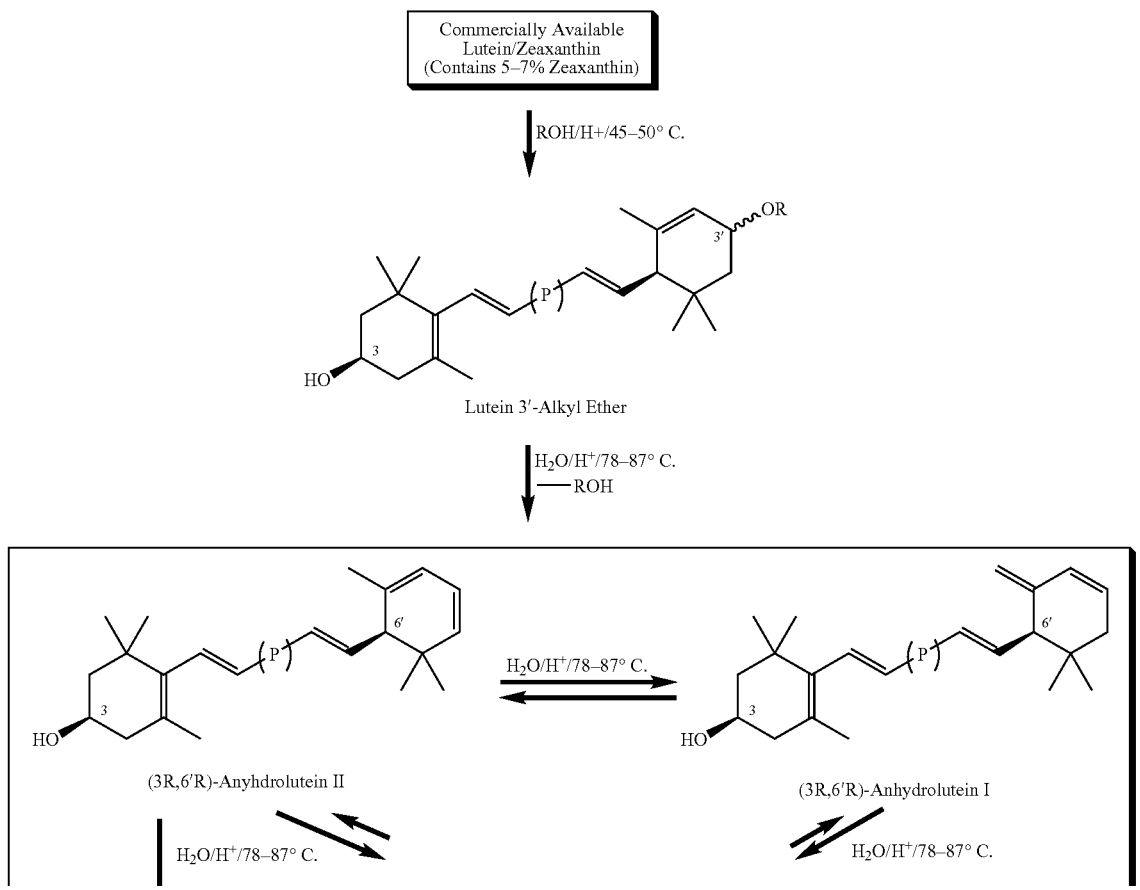

SCHEME 2

Two-steps production of (3R)-β-cryptoxanthin (major product) and (3R,6'R)-α-cryptoxanthin (minor product) by acid-catalyzed dehydration of (3R,3'R,6'R)-lutein in an alcohol at elevated temperatures followed by ionic hydrogenation of anhydroluteins.

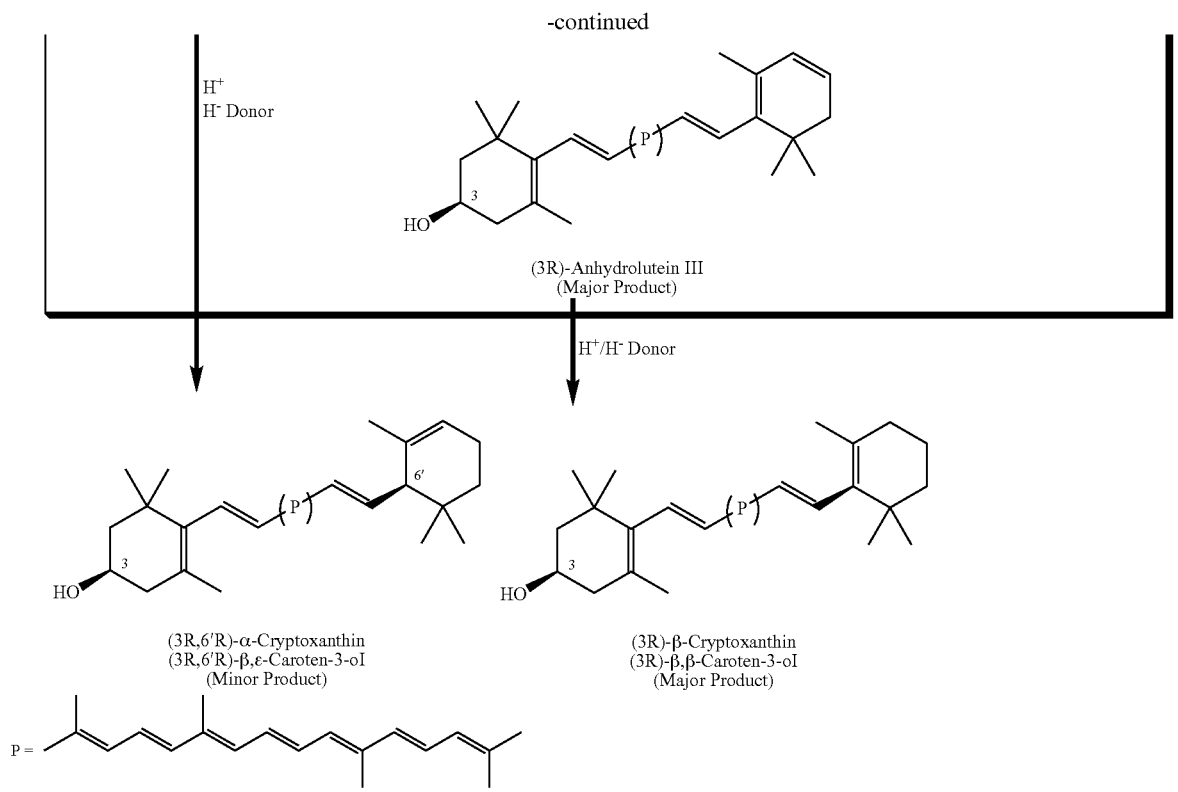

DETAILED DESCRIPTION OF THE INVENTION

In one embodiment of the present invention, commercially available (3R,3'R,6'R)-lutein (containing 5–7% (3R,3'R)-zeaxanthin) reacts with an alcohol, employed as solvent, in the presence of catalytic amount of an acid at 45–50° C. to give the corresponding lutein 3'-alkyl ethers (Scheme 2). At the beginning of the acid-catalyzed dehydration reaction, (3R,3'R,6'R)-lutein exists as a suspension in alcohol. However, once the corresponding lutein 3'-alkyl ethers are formed, a uniform solution is obtained. If the temperature of the solution is increased above 50° C., acid-catalyzed elimination of alcohol from lutein 3'-alkyl ethers results in a mixture of anhydroluteins in which anhydrolutein I is the major product and anhydroluteins II and III are the minor products. Further heating of this solution between 78–87° C. results in acid-catalyzed isomerization of anhydroluteins I and II to anhydrolutein III. In this homogenous solution, the isomerization is also accompanied by the formation of substantial amounts of Z(cis)-anhydroluteins. These Z(cis)-anhydroluteins are converted to their all-E-isomers in a heterogeneous system in the presence of water when heated between 78–87° C.

In an alternative embodiment, the lutein 3'-alkyl ethers are formed below 50° C. and water is added to lower the solubility of lutein 3'-alkyl ethers. Additional amounts of acid is added and the reaction temperature raised to about 78–87° C. to form the dehydration products of (3R,3'R,6'R)-lutein with the loss of the corresponding alcohol. Under these conditions, anhydrolutein I is formed as the major product and anhydroluteins II and III are the minor products. After continuous heating at an elevated temperature in the range of 78–87° C. for up to 7–20 h, anhydrolutein I and II gradually undergo isomerization to form anhydrolutein III. Substantially no E/Z(trans/cis)-isomerization of these carotenoids at elevated temperatures takes place. If water is added at the beginning of the reaction, the dehydration of (3R,3'R,6'R)-lutein does not proceed to completion and results in an epimeric mixture of (3R,3'R,6'R)-lutein and (3R,3'S,6'R)-lutein (3'-epilutein).

In an alternative embodiment of the invention, a combination of the above methods are employed to reduce the reaction time. In this approach, a considerable amount of anhydrolutein III is prepared at 78–87° C. before addition of water (method 1) and then water and additional amounts of acid is added and heating is continued to complete the conversion of anhydroluteins I and II to anhydrolutein III (Method 2).

Depending on the nature and the boiling point of the alcohol, length of heating, and the concentration of acid, the relative ratio of anhydrolutein III to anhydrolutein I and II can be readily manipulated by the methods described earlier. During these processes, anhydroluteins I and II are not completely isomerized to anhydrolutein III. For example, when 1-propanol is used as the alcohol and the reaction mixture is heated at 87–87° C. for 20 h by Method 2, the relative distribution of anhydroluteins is: anhydrolutein III (84%), anhydrolutein I (10%), and anhydrolutein II (6%). The present invention will further demonstrate that a mixture of anhydrolutein with a high concentration of anhydrolutein III can be converted to a mixture of all-E-cryptoxanthins with a high concentration of (all-E, 3R)-β-cryptoxanthin.

In the second step, the dehydration products of (3R,3'R,6'R)-lutein undergo ionic hydrogenation with a strong acid and a hydride ion donor at ambient temperature to yield (3R)-β-cryptoxanthin and (3R,6'R)-α-cryptoxanthin as major and minor products, respectively. This step can be carried out with the crude product after removal of water and alcohols by filtration or alternatively anhydroluteins can be first isolated and purified prior to ionic hydrogenation.

The commercially available (3R,3'R,6'R)-lutein employed in these reactions may be isolated from extracts of marigold flowers and may contain approximately 5–7% (3R,3'R)-zeaxantlhin. Because (3R,3'R)-zeaxanthin does not react with acids or hydride ion donors/acid, this carotenoid can be recovered in the final product.

Reagents and Starting Materials

Two types of (3R,3'R,6'R)-lutein may be employed as starting materials in this invention, these are: 1) commercially available (3R,3'R,6'R)-lutein with approximately 85% total carotenoid purity and 2) crystalline lutein with greater than 97% total carotenoid purity according to the process described in WO 99/20587. Both starting materials are prepared from crude saponified extracts of Marigold flowers and contain approximately 5–7% (3R,3'R)-zeaxanthin. Mixtures of these two starting materials may also be employed.

The crude saponified extract of Marigold flower containing (3R,3'R,6'R)-lutein and several minor carotenoids may be prepared according to the process described in WO 99/20587. (3R,3'R,6'R)-Lutein (97% total carotenoid purity) containing approximately 5–7% zeaxanthin may also be purified from this extract according to this procedure. Commercially available (3R,3'R,6'R)-lutein (85% total carotenoid) may be obtained from Kemin Industries (Des Moines, Iowa). All reagents used in this invention are commercially available (Aldrich Chemical Co., Milwaukee, Wis.) and are used without further purification. The carotenoid composition of the 85% and 97% lutein is shown in Table 1.

TABLE 1

Carotenoid composition of 85% and 97% (3R,3'R,6'R)-lutein isolated from marigold flowers.

| Marigold Carotenoids | Composition | |
| --- | --- | --- |
| | 85% total carotenoid purity | 97% total carotenoid purity |
| (all-E,3R,3'R,6'R)-lutein[a] | 91.0 | 95.0 |
| (all-E,3R,3'R)-zeaxanthin | 6.54 | 5.0 |
| Anhydroluteins (lutein dehydration products) | 0.43 | 0.0 |
| β-carotene | 0.35 | 0.0 |
| α-cryptoxanthin | 0.41 | 0.0 |
| β-cryptoxanthin | 0.38 | 0.0 |
| 3-hydroxy-β,ε-caroten-3'-one | 0.89 | 0.0 |
| Total | 100.0 | 100.0 |

[a]The 85% and 97% lutein did not contain any significant amount of Z (cis)-luteins.

Acid-Catalyzed Dehydration of (3R,3'R,6'R)-Lutein to Anhydroluteins at Elevated Temperatures by Method 1

In a typical experiment, a suspension of 85% commercially available (3R,3'R,6'R)-lutein (1.0 g of 85% pure, 0.85 g, 1.49 mmol) in 30 ml of an alcohol is treated with 0.2–0.8 ml of 50% sulfuric acid/water (v/v). The mixture is heated to an elevated temperature. The mixture is heated at the elevated temperature of about 78–87° C. for 0.5–4 h. Depending on the nature of the alcohol and the length of heating, (3R,3'R,6'R)-lutein is converted to a mixture of E/Z(trans/cis)-anhydroluteins in which E/Z(trans/cis)-anhydrolutein III is the major product. Water (40 ml) is added and heating is continued at an elevated temperature of about 78–100° C. until the Z-isomers of anhydroluteins are converted to their all-E-isomers and the mixture arrives at equilibrium. This isomerization can be followed by an HPLC method that has been previously described by Khachik et al. *J. Chrom. Biomed. Appl.*, 670:219–233, (1995). Virtually all alcohols or their combinations with no limitation can be employed. These include: ethanol, 1-propanol, 2-propanol, 1-butanol, 2-butanol, isobutyl alcohol, tert-butyl alcohol, 1-pentanol (n-amyl alcohol), 2-n-hexyl alcohol, n-octyl alcohol, ethylene glycol, propylene glycol, propylene glycol, Some of these alcohols form an azeotropic mixture with water and as a result the boiling point of the solutions in most cases is in the range of 78–100° C. The acid can be sulfuric acid, hydrochloric acids, phosphoric acid and the like. A strong organic acid such as trifluoroacetic acid may also be employed. A small amount of Z-isomers of the anhydroluteins formed during this reaction can be removed by simply filtering the aqueous alcoholic solution of the product or by isolation and crystallization of anhydroluteins prior to conversion of this carotenoid to (3R,6'R)-β-cryptoxanthin and (3R)-α-cryptoxanthin. A summary of some of the acid-catalyzed dehydration reactions of (3R,3'R,6'R)-lutein to anhydrolutein III in various alcohols is shown in Table 2.

TABLE 2

The products of acid-catalyzed dehydration of (3R,3'R,6'R)-lutein (containing 5–7% (3R,3'R)-zeaxanthin) with sulfuric acid in various alcohols according to Method 1.

| Lutein (85%), g Containing 5–7% Zeaxanthin (Reaction Time, h)[a] | Alcohol, ml 50% $H_2SO_4/H_2O$ (v/v) (ml)[b] | Temp ° C. | Recovered Zeaxanthin (%) | all-E-Anhydroluteins (%) | | |
| --- | --- | --- | --- | --- | --- | --- |
| | | | | I | II | III |
| 1.00 (4 h) | Ethanol, 30 ml 0.8 ml | 78 | 14 | 19 | 23 | 44 |
| 1.00 (0.5 h) | 1-Propanol, 30 ml 0.2 ml | 87 | 9 | 25 | 21 | 45 |
| 1.00 (2 h) | 2-Propanol, 30 ml 0.8 ml | 80 | 12 | 16 | 23 | 49 |

[a]Indicates the time needed for conversion of lutein to E/Z-anhydroluteins; an additional 4–5 h of heating under reflux is needed to convert the E/Z-anhydroluteins to all-E-anhydroluteins.
[b]In all cases, 50% $H_2SO_4/H_2O$ (v/v) was first added at 78–87° C. and water (40 ml) was added after substantial amounts of E/Z-anhydrolutein III was formed.

The work-up of the acid-catalyzed dehydration of (3R, 3'R,6'R)-lutein to anhydroluteins is as follows. The reaction mixture is cooled to ambient temperature or lower, preferably in the range of about 5–10° C., and the solids are collected by filtration. The solids are washed with a small amount of an alcohol (e.g. ethanol) and directly used for the preparation of (3R,6'R)-β-cryptoxanthin and (3R)-α-cryptoxanthin in the next step.

A more elaborate work-up consists of isolation and purification of anhydroluteins prior to their transformation to (3R,6'R)-β-cryptoxanthin and (3R)-α-cryptoxanthin. According to this method, the crude mixture of anhydroluteins is neutralized with an aqueous mineral base such as potassium or sodium hydroxide and the product is dissolved in an organic solvent immiscible with water (ethyl acetate, tert-butyl methyl ether, dichloromethane, 1,2-dichloroethane). After removing the base by washing the organic layer with water, the solvents are evaporated and the anhydroluteins are crystallized from an alcohol.

Therefore the invention relates to a method of reacting (3R,3'R,6'R)-lutein with a catalytic amount of an acid to obtain a mixture of anhydroluteins, comprising reacting (3R,3'R,6'R)-lutein with an alcohol that is also used as the solvent in the presence of catalytic amount of an acid above ambient temperature, preferably between 78–87° C., until the product is enriched in E/Z-anhydrolutein III, adding water and further heating at this temperature until Z-isomers of anhydroluteins are mostly converted to their all-E-counterparts. In a preferred embodiment, the reaction comprises:

a) suspending commercially available (3R,3'R,6'R)-lutein containing 5–7% (3R,3'R)-zeaxanthin in an appropriate volume (about 3 ml solvent/100 mg lutein) of an alcohol and adding catalytic amount of an aqueous acid (e.g. 0.2–0.8 ml of 50% $H_2SO_4$/water (v/v) per g of lutein) to obtain a mixture;

b) stirring the mixture at 78–87° C. for about 0.5–4 hours to obtain a mixture of anhydroluteins rich in anhydrolutein III;

c) adding water (e.g. about 40 ml/g of lutein) and more aqueous acid (e.g. about 0.4–0.8 ml of 50% $H_2SO_4$/water (v/v) per g of lutein) if needed and heating the mixture between 78–87° C. to obtain a mixture of all-E-anhydroluteins in which all-E-anhydrolutein III is the major product;

d) cooling down the product to ambient temperature or below, preferably at about 5–10° C. to obtain a crystalline mixture of anhydroluteins;

e) filtering and washing the crystals with an alcohol or acetone; collecting the crystals and transforming the crude mixture of anhydroluteins directly to (3R)-β-cryptoxanthin and (3R,6'R)-α-cryptoxanthin in the next step without further purification.

Alternatively, the crude reaction mixture is worked up and the product is crystallized to give a mixture of anhydroluteins. In a preferred embodiment, the work-up and crystallization of the product comprises:

adding a base to neutralize the acid and dissolving the product in an organic solvent immiscible with water (e.g. ethyl acetate, tert-butyl ethyl ether, dichloromethane, 1,2-dichloroethane);

washing the organic layer with water to remove the base and evaporating the solvent to obtain a concentrated residue containing anhydroluteins;

crystallizing anhydroluteins from an alcohol; collecting and drying the crystals, e.g. under high vacuum at about 60° C.

Acid-Catalyzed Dehydration of (3R,3'R,6'R)-Lutein to Anhydroluteins at Elevated Temperatures by Method 2

In a typical experiment, a suspension of 85% commercially available (3R,3'R,6'R)-lutein (1.0 g of 85% pure, 0.85 g, 1.49 mmol) in 30 ml of an alcohol such as 1-propanol is treated with 0.2 ml of 50% sulfuric acid/water (v/v) and the mixture is heated to an elevated temperature in the range of about 45–50° C. for 1–2 h. Small amounts of a concentrated acid is added at first since the presence of excess water at the beginning of the reaction prevents the formation of lutein 3'-alkyl ether. Depending on the nature of the alcohol, (3R,3'R,6'R)-lutein is converted to its 3'-alkyl ether within 1–2 h. Water (40 ml) followed by 0.4–0.8 ml of 50% sulfuric acid/water (v/v) is added and the temperature of the mixture is increased to 78–87° C. The heating is continued until most of the anhydrolutein I and II are converted to anhydrolutein III and the mixture arrives at an equilibrium. When 1-propanol is used as the reacting alcohol and solvent, the final product contains approximately 84% anhydrolutein III, 10% anhydrolutein I, and 6% anhydrolutein II. Depending on the nature of the alcohol, temperature, and the concentration of the acid, the duration of the reactions may vary between 7–20 hours. The alcohols described in method 1 can all be used. Because of the high solubility of anhydroluteins in certain alcohols at elevated temperature, the isomerization of anhydroluteins I and II to anhydrolutein III in some cases is accompanied by E/Z(trans/cis)-isomerization. A summary of some of the acid-catalyzed dehydration reactions of (3R,3'R,6'R)-lutein to anhydrolutein III in various alcohols by Method 2 is shown in Table 3.

TABLE 3

The products of acid-catalyzed dehydration of (3R,3'R,6'R)-lutein (containing 5–7% (3R,3'R)-zeaxanthin) with sulfuric acid in various alcohols at elevated temperatures according to Method 2.

| Lutein (85%), g Containing 5–7% Zeaxanthin (Reflux Time, h) | Alcohol, ml $H_2O$, ml 50% $H_2SO_4/H_2O$ (v/v) (ml)[a] | Reflux Temp ° C. | Recovered Zeaxanthin (%) | all-E-Anhydroluteins (%) | | |
|---|---|---|---|---|---|---|
| | | | | I | II | III |
| 1.00 (20 h) | 1-Propanol, 30 ml $H_2O$, 40 ml 0.6 ml | 87 | 2 | 10 | 6 | 82 |
| 1.00 (7 h) | 1-Propanol, 30 ml $H_2O$, 40 ml 0.8 ml | 87 | 7 | 16 | 11 | 66 |
| 1.00 (11 h) | 1-Propanol, 30 ml $H_2O$, 40 ml 1.0 ml | 87 | 4 | 35 | 13 | 48 |
| 1.00 (4 h) | 2-Propanol, 30 ml $H_2O$, 40 ml 1.0 ml | 80 | 9 | 57 | 9 | 25 |
| 1.00 (6 h) | Ethanol, 30 ml $H_2O$, 40 ml 0.8 ml | 78 | 7 | 57 | 8 | 28 |
| 1.00 (2 h) | 1-Butanol, 30 ml $H_2O$, 40 ml 0.4 ml | 93 | 9 | 47[b] | 12[b] | 32[b] 18% (E) 14% (Z) |

TABLE 3-continued

The products of acid-catalyzed dehydration of (3R,3'R,6'R)-
lutein (containing 5–7% (3R,3'R)-zeaxanthin) with sulfuric acid in various
alcohols at elevated temperatures according to Method 2.

| Lutein (85%), g Containing 5–7% Zeaxanthin (Reflux Time, h) | Alcohol, ml H$_2$O, ml 50% H$_2$SO$_4$/H$_2$O (v/v) (ml)[a] | Reflux Temp ° C. | Recovered Zeaxanthin (%) | all-E-Anhydroluteins (%) | | |
|---|---|---|---|---|---|---|
| | | | | I | II | III |
| 1.00 (2 h) | 2-Butanol, 30 ml H$_2$O, 40 ml 1.0 ml | 87 | 8 | 56[b] | 11[b] | 25[b] 13% (E) 12% (Z) |
| 1.00 (5 h) | tert-Butyl alcohol, 30 ml H$_2$O, 40 ml 0.8 ml | 83 | 7 | 48 | 10 | 35 |

[a]Indicates the total amount of acid used; in all cases, 0.2 ml of 50% H$_2$SO$_4$/H$_2$O (v/v) was first added at 50° C. and the remainder of the acid and water (40 ml) were added after lutein 3'-alkyl ethers were formed.
[b]Due to solubility of anhydroluteins in 1-butanol, 2-butanol, and tert-butyl alcohol at the reflux temperature, considerable amount of Z-isomer of anhydroluteins were formed.

The work-up of the acid-catalyzed dehydration of (3R, 3'R,6'R)-lutein to anhydroluteins by this method is identical to that described in Method 1.

Conversion of Anhydroluteins to (3R)-β-Cryptoxanthin and (3R,6'R)-α-Cryptoxanthin by Ionic Hydrogenation with Borane-Anine/TFA The crude or purified mixture of anhydroluteins that has a high concentration of anhydrolutein III (prepared by methods 1 or 2) reacts with borane-amine complexes such as borane-trimethylamine (Me$_3$N.BH$_3$) or borane-dimethylamine (Me$_2$NH.BH$_3$), or borane-tert-butylamine (Me$_3$CNH$_2$.BH$_3$) complexes in the presence of an acid, preferably trifluoroacetic acid (TFA), at ambient temperature in a chlorinated solvent (e.g. dichloromethane, 1,2-dichloroethane) to give a mixture of (3R)-β-cryptoxanthin as the major product and (3R,6'R)-α-cryptoxanthin as the minor product in excellent yields within 1–3 hours. Other hydride ion donors that can be used in the present invention include trialkylsilanes including trimethylsilane and triethylsilane. The 5–7% of (3R,3'R)-zeaxanthin that is present in the starting material does not react with borane-amine complex/TFA and can be recovered in the product.

In a typical experiment, a solution of anhydroluteins (1.1 mmol) in dichloromethane (20 ml) is first treated with 1.37 mmol of borane-amine complex and this is followed by the addition of TFA (3.89 mmol). The mixture is stirred at ambient temperature for 1–3 hours. This results in a mixture of E/Z(trans/cis)-isomers of (3R)-β-cryptoxanthin and (3R, 6'R)-α-cryptoxanthin. The solvent is displaced with an alcohol and water and the mixture is heated at about 78–87° C. to convert the Z-isomers of these carotenoids to their all-E-isomer. The work-up consists of neutralizing the acid with a base and extracting the product with an organic solvent immiscible with water (e.g. ethyl acetate, tert-butyl ethyl ether, dichloromethane, 1,2-dichloroethane) and crystallizing the product from an alcohol to obtain all-E-(3R)-β-cryptoxanthin (major product) and all-E-(3R,6'R)-α-cryptoxanthin (minor product).

Therefore the invention relates to a method of converting crude or a purified mixture of anhydroluteins rich in anhydrolutein III to (3R)-β-cryptoxanthin (major product) and (3R,6'R)-α-cryptoxanthin (minor product), comprising reacting anhydroluteins, Me$_3$N.BH$_3$ or Me$_2$NH.BH$_3$ or Me$_3$CNH$_2$.BH$_3$ or other borane-amine complexes, or hydride donors, and an acid in a chlorinated solvent, preferably dichloromethane, at ambient temperature. In a preferred embodiment, the reaction comprises:

dissolving anhydroluteins containing (3R,3'R)-zeaxanthin in an appropriate volume (e.g. about 2 ml solvent/100 mg anhydrolutein) of dichloromethane and adding about 1.3 mol equivalent of borane-amine complex then adding about 3.5–4 mol equivalent of TFA to obtain a mixture;

stirring the mixture at ambient temperature for about 1–3 hours;

displacing the chlorinated solvent with an alcohol and water heating the mixture at 78–87° C. to convert the Z-isomers of cryptoxanthins to their all-E-counterparts;

adding an aqueous solution of a base (e.g. sodium bicarbonate) to neutralize the acid, extracting with an organic solvent, and crystallizing the residue from alcohol;

collecting the crystals, e.g. by filtration or on a centrifuge, and washing the crystals with an alcohol or acetone;

drying the crystals, e.g. under high vacuum at about 60° C., to obtain a mixture of recovered (3R,3'R)-zeaxanthin, all-E-(3R)-β-cryptoxanthin (major product) and all-E-(3R, 6'R)-α-cryptoxanthin (minor product).

Extractions are performed with any organic solvent. Preferred organic solvents include ethyl acetate, an ether, or a chlorinated solvent.

Various alcohols can be used in the present invention, including but not limited to C$_{1-10}$ alcohols such as methanol, ethanol, 1-propanol, 2-propanol, 1-butanol, 2-butanol, isobutyl alcohol, tert-butyl alcohol, 1-pentanol, 2-pentanol, n-hexyl alcohol, n-octyl alcohol, ethylene glycol, and propylene glycol. Various aqueous mineral acids can be used in the present invention, including but not limited to aqeuous sulfuric, hydrochloric, hydrobromic, hydrofluoric, nitric, and phosphoric acid. Various strong organic acids can be used in the present invention, including but not limited to trifluoroacetic, trichloroacetic, and chloroacetic acid.

"Elevated temperature" as used here is meant to be any temperature in the range of about 45–100° C.

"Substantially no isomerization" is used herein to mean that at least greater than about 95% of a product or starting material is present in the all-trans or all-E confirmation.

"Substantially no Z-isomers" is used herein to mean that at least greater than about 95% of a product or starting material is present in the all-trans or all-E confirmation.

As used herein, the term "about" means that number referred to as having "about" comprises the recited number plus or minus up to 10% of that number. For example, "about 5 hours" includes 4.5 to 5.5 hours. "About 0° C." includes −10° C., 0° C. and +10° C.

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLE 1

Conversion of (3R,3'R,6'R)-Lutein (85% pure) to Anhydroluteins I, II, and III with Sulfuric Acid in Ethanol Using Method 1

A suspension of (3R,3'R,6'R)-lutein (1.0 g of 85% pure, 1.49 mmol) in 30 ml of ethanol was treated with 50% (v/v) sulfuric acid/water (0.80 ml) and the mixture was heated to reflux (78–80° C.). Shortly after, a dark red solution was obtained. The course of the reaction was followed by HPLC. After 4 h, water (40 ml) was added and reflux continued at 78–80° C. for 4 h until most of the Z-anhydroluteins were converted to all-E-anhydroluteins. The mixture was allowed to cool down to room temperature and the product was collected by filtration. The red crystals were washed with 15 ml of ethanol, and dried under high vacuum at 60° C. to give 0.85 g of anhydroluteins (85% pure, 0.72 g, 1.3 mmol; 87%) which was shown by HPLC to consist of anhydrolutein III (44%), anhydrolutein II (23%), (3R,6'R)-anhydrolutein I (19%), and unreacted (3R,3'R)-zeaxanthin (14%). This mixture was used in subsequent reactions with $Me_3N.BH_3$/TFA without further purification.

EXAMPLE 2

Conversion of Anhydroluteins from Method 1 to (3R)-β-Cryptoxanthin and (3R,6'R)-α-Cryptoxanthin with $Me_3N.BH_3$/Trifluoroacetic Acid (TFA) in Dichloromethane A solution of anhydroluteins prepared in Example 1 (0.85 g of 85% pure, 0.72 g, 1.3 mmol) in dichloromethane (20 ml) was first treated with borane-trimethylamine complex (0.126 g, 1.73 mmol) followed by trifluoroacetic acid (0.40 ml, 0.592 g, 5.19 mmol). The mixture was stirred at ambient temperature and the course of the reaction was followed by HPLC. After 3 h, the product was treated with 20 ml of 2% sodium bicarbonate (20 ml). The organic layer was removed, washed with water (20 ml), and dried over sodium sulfate. The dichloromethane was displaced with ethanol (30 ml) and the mixture was heated under reflux for 2 h until most of Z(cis)-cryptoxanthins were shown by HPLC to have converted to their all-E(trans)-isomers and the mixture arrived at an equilibrium. The solution was allowed to cool down to room temperature and the crystals were removed by filtration and washed with 10 ml of cold ethanol. After drying under high vacuum at 60° C., the dark orange product was shown by BPLC to contain 0.67 g (80% pure) of total carotenoids consisting of a mixture of (3R)-β-cryptoxanthin (55%), (3R,6'R)-α-cryptoxanthin (30%), anhydrolutein II (8%), and (3R,3'R)-zeaxanthin (7%).

EXAMPLE 3

Conversion of (3R,3'R,6'R)-Lutein (85% pure) to Anhydroluteins I, II, and III with Sulfuiric Acid in 1-Propanol Using Method 2

A suspension of (3R,3'R,6'R)-lutein (1.0 g of 85% pure, 1.49 mmol)) in 30 ml of 1-propanol was treated with 50% (v/v) sulfuric acid/water (0.20 ml) and the mixture was heated to 50° C. for 1 h until a dark red solution was obtained and all the starting material was completely converted to lutein 3'-propyl ether. At this time only the unreacted (3R,3'R)-zeaxanthin was shown to be present by HPLC. Water (40 ml) was added followed by 50% (v/v) sulfuric acid/water (0.40 ml) and the temperature of the solution was increased to 87° C. After 20 h, the mixture was allowed to cool down to room temperature and the product was treated with 3 ml of a 9M solution of potassium hydroxide (prepared from 50.5 g of KOH in 100 ml of water) and ethyl acetate (40 ml). The organic layer was removed, washed twice with 2×40 ml of water, and dried over sodium sulfate. Nearly all of the ethyl acetate was evaporated under reduced pressure below 40° C. and the residue was treated with ethanol (30 ml) and cooled to 5–10° C. until anhydroluteins crystallized. The crystals were removed by filtration, washed with 15 ml of ethanol, and dried under high vacuum at 60° C. to give 0.85 g (85% pure, 0.72 g, 1.3 mmol; 87%) of a dark red product which was shown by HPLC to contain a mixture of anhydroluteins and recovered (3R,3'R)-zeaxanthin. The relative distribution of carotenoids in this product was: anhydrolutein III (82%), (3R,6'R)-anhydrolutein I (10%), anhydrolutein II (6%), and unreacted (3R,3'R)-zeaxanthin (2%). Substantially no Z(cis)-isomers of anhydroluteins were detected in the final product. This mixture was used in subsequent reactions with $Me_3N.BH_3$/TFA without further purification.

EXAMPLE 4

Conversion of Anhydroluteins from Method 2 to (3R)-β-Cryptoxanthin and (3R,6'R)-α-Cryptoxanthin with $Me_3N.BH_3$/Trifluoroacetic Acid (TFA) in Dichloromethane A solution of anhydroluteins prepared in Example 3 (0.85 g of 85% pure, 0.72 g, 1.3 mmol) in dichloromethane (20 ml) was first treated with borane-trimethylamine complex (0.114 g, 1.56 mmol) followed by trifluoroacetic acid (0.36 ml, 0.533 g, 4.67 mmol). The mixture was stirred at ambient temperature and the course of the reaction was followed by HPLC. After 3 h, the product was treated with 20 ml of 2% sodium bicarbonate (20 ml). The organic layer was removed, washed with water (20 ml), and dried over sodium sulfate. The dichloromethane was displaced with ethanol (30 ml) and the mixture was heated under reflux for 2 h until most of Z(cis)-cryptoxanthins were shown by HPLC to have converted to their all-E(trans)-isomers and the mixture arrived at an equilibrium. The solution was allowed to cool down to room temperature and the crystals were removed by filtration and washed with 10 ml of cold ethanol. After drying under high vacuum at 60° C., the dark orange product was shown by HPLC to contain 0.60 g (80% pure) of total carotenoids consisting of a mixture of (3R)-β-cryptoxanthin (61%), (3R,6'R)-α-cryptoxanthin (18%), aiihydrolutein II (10%), anhydrolutein III (7%), and (3R,3'R)-zeaxanthin (4%). II (10%).

EXAMPLE 5

Conversion of (3R,3'R,6'R)-Lutein (85% pure) to Anhydroluteins I, II, and III with Sulfuiric Acid in 2-Propanol Using Method 1

A suspension of (3R,3'R,6'R)-lutein (1.0 g of 85% pure≈0.85 g, 1.49 mmol)) in 30 ml of 2-propanol was treated with 50% (v/v) sulfuric acid/water (0.80 ml) and the mixture was heated to reflux (80–82° C.). After 2 h, water (40 ml) was added and reflux continued at 80–82° C. for 4 h until most of the Z-anhydroluteins were converted to all-E-anhydroluteins. The mixture was allowed to cool down to room temperature and the product was treated with 6 ml of a 9M solution of potassium hydroxide (prepared from 50.5 g of KOH in 100 ml of water) and ethyl acetate (40 ml). The organic layer was washed with water (2×30 ml) and dried over sodium sulfate. Most of the solvent was evaporated and the residue in about 10 ml of solvent was treated with ethanol (30 ml) and allowed to stand at 5–10° C. until anhydroluteins crystallized. The red crystals were collected by filtration, washed with 15 ml of ethanol, and dried under high vacuum at 60° C. to give 0.80 g of anhydroluteins (85% pure, 0.68 g, 1.24 mmol; 83%) which was shown by HPLC to consist of anhydrolutein III (49%), anhydrolutein II (23%), (3R,6'R)-anhydrolutein I (16%), and unreacted (3R, 3'R)-zeaxanthin (12%).

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:

1. A process for converting (a) (3R,3'R,6'R)-lutein (85% total carotenoids) or (b) purified lutein (97% total carotenoids) containing 5–7% (3R,3'R)-zeaxanthin or mixtures of (a) and (b) to a mixture of anhydroluteins I, II, and III at elevated temperature, comprising reacting (3R,3'R,6'R)-lutein in an alcohol or mixture of alcohols with a catalytic amount of an aqueous mineral acid or a strong organic acid at an elevated temperature of about 45° C. to about 100° C. to give a mixture of anhydroluteins comprising anhydrolutein III as the major product, anhydroluteins I and II as the minor products, and the recovered (3R,3'R)-zeaxanthin.

2. The process of claim 1, wherein said mixture of anhydroluteins comprises at least 80% anhydrolutein III.

3. The process of claim 2, wherein said anhydrolutein III comprises substantially no Z-anhydrolutein III.

4. The process of claim 1, wherein said alcohol is selected from the group consisting of ethanol, 1-propanol, 2-propanol, 1-butanol, 2-butanol, isobutyl alcohol, tert-butyl alcohol, 1-pentanol (n-amyl alcohol), 2-pentanol, n-hexyl alcohol, n-octyl alcohol, ethylene glycol, and propylene glycol.

5. The process of claim 1, wherein said aqueous mineral acid is aqueous sulfuric, hydrochloric or phosphoric acid, and said strong organic acid is trifluoroacetic or trichloroacetic acid.

6. The process of claim 1, wherein said elevated temperature is 78–100° C.

7. The process of claim 1, further comprising adding water to convert Z(cis)-isomers of anhydroluteins at the elevated temperature to all-E-anhydrolutein rich in all-E-anhydrolutein III.

8. The process of claim 1, further comprising isomerizing anhydroluteins I and II to anhydrolutein III at elevated temperatures in the presence of water and acid.

9. The method of claim 1, further comprising cooling the mixture of anhydroluteins to ambient temperature or between 5–10° C. to precipitate the all-E-anhydroluteins as a crystalline product.

10. The method of claim 9, further comprising filtering and washing the crystalline product with an alcohol or acetone and drying at about 60° C. under high vacuum.

11. The method of claim 9, further comprising reacting all-E-anhydroluteins with a chlorinated solvent, hydride donor and a strong organic acid to give a mixture of all-E-(3R)-β-cryptoxanthin and all-E-(3R,6'R)-α-cryptoxanthin.

12. The method of claim 1, wherein the mixture of anhydroluteins is neutralized with an aqueous or an organic base, extracted with an organic solvent, and crystallized from an alcohol.

13. The method of claim 12, wherein the organic solvent is ethyl acetate, an ether, or a chlorinated solvent.

14. A process for converting (a) (3R,3'R,6'R)-lutein (85% total carotenoids) or (b) purified lutein (97% total carotenoids) containing 5–7% (3R,3'R)-zeaxanthin or mixtures of (a) and (b) to lutein 3'-alkyl ether, comprising reacting (3R,3'R,6'R)-lutein with an alcohol in the presence of a catalytic amount of an aqueous mineral acid or a strong organic acid at an elevated temperature to give all-E(trans)-lutein 3'-alkyl ether and the recovered (3R,3'R)-zeaxanithin.

15. The process of claim 14, wherein said alcohol is ethanol, 1-propanol, 2-propanol, 1-butanol, 2-butanol, isobutyl alcohol, tert-butyl alcohol, 1-pentanol (n-amyl alcohol), 2-pentanol, n-hexyl alcohol, n-octyl alcohol, ethylene glycol, or propylene glycol.

16. The process of claim 14, wherein said aqueous mineral acid is aqueous sulfuric, hydrochloric or phosphoric acid, and said strong organic acid is trifluoroacetic or trichloroacetic acid.

17. The process of claim 14, wherein said elevated temperature is 45–50° C.

18. The method of claim 14, further comprising transforming the lutein 3'-alkyl ether in situ into a mixture of anhydroluteins, comprising reacting lutein 3'-alkyl ether with a catalytic amount of an aqueous mineral acid or a strong organic acid at an elevated temperature in water to give anhydrolutein III as the major product and anhydroluteins I and II as minor products.

19. The method of claim 18, wherein the aqueous mineral acid is aqueous sulfuric, hydrochloric or phosphoric acid, and the strong organic acid is trifluoroacetic acid.

20. The process of claim 18, wherein the elevated temperature is 78° C. to about 100° C.

21. The process of claim 18, further comprising adding water thereby preventing E/Z(trans/cis)-isomerization of anhydroluteins at an elevated temperature of 78° C. to about 100° C.

22. The process of claim 18, further comprising isomerizing anhydroluteins I and II to anhydrolutein III at elevated temperatures in the presence of water in 7–20 h.

23. The method of claim 18, further comprising cooling said mixture of anhydroluteins to ambient temperature or between 5–10° C. to precipitate the all-E-anhydroluteins as a crystalline product.

24. The method of claim 18, further comprising filtering said crystalline product, washing said product with an alcohol or acetone, and drying said product at 60° C. under high vacuum.

25. The method of claim 24, further comprising reacting said product with a chlorinated solvent, hydride donor and a strong organic acid to give a mixture of all-E-(3R)-β-cryptoxanthin and all-E-(3R,6'R)-α-cryptoxanthin.

26. The method of claim 14, wherein said all-E(trans)-lutein 3'-alkyl ether is neutralized with an aqueous or an organic base, extracted with an organic solvent, and crystallized from an alcohol.

27. The method of claim 26, wherein the organic solvent is ethyl acetate, an ether or a chlorinated solvent.

28. A process for converting a mixture of all-E-anhydroluteins rich in all-E-anhydrolutein III, to a mixture of all-E-(3R)-β-cryptoxanthin and all-E-(3R,6'R)-α-cryptoxanthin, comprising reacting anhydroluteins containing 3–8% (3R,3'R)-zeaxanthin in a chlorinated solvent with about 1.3 equivalent of a hydride donor and about 3.5–4 equivalent of a strong organic acid at ambient temperature for about 1–5 hours to give a mixture of E/Z-(3R)-β-cryptoxanthin, E/Z-(3R,6'R)-α-cryptoxanthin, unreacted E/Z-anhydroluteins, and recovered E/Z-(3R,3'R)-zeaxanthin.

29. The method of claim 28, wherein said hydride ion donor is borane-trimethylamine, borane-dimethylamine, or borane-tert-butylamine.

30. The method of claim 28, wherein said hydride ion donor is a trialkylsilanes.

31. The method of claim 30, wherein said trialkylsilanes is triethylsilane.

32. The method of claim 28, wherein said strong organic acid is trifluoroacetic acid.

33. The method of claim 28, further comprising heating said mixture of E/Z-(3R)-β-cryptoxanthin, E/Z-(3R,6'R)-α-cryptoxanthin, unreacted E/Z-anhydroluteins, and recovered E/Z-(3R,3'R)-zeaxanthin in an alcohol at 78–87° C. to convert the Z-carotenoids to their all-E-isomers and obtain a mixture of all-E-(3R)-β-cryptoxanthin, all-E-(3R,6'R)-α-cryptoxanthin, unreacted all-E-anhydroluteins, and recovered all-E-(3R,3'R)-zeaxanthin.

34. The method of claim 33, wherein said alcohol is ethanol, 1-propanol, or 2-propanol.

35. The method of claim 33, further comprising neutralizing said all-E-isomers with an aqueous or an organic base, removing the aqueous layer, and displacing the chlorinated solvent with a higher boiling alcohol by distillation under reduced pressure until carotenoids crystallize from the alcohol.

36. The method of claim 35, further comprising crystallizing carotenoids, collecting said carotenoids, washing said carotenoids with acetone or alcohol and drying said carotenoids under high vacuum at 60° C.

* * * * *

UNITED STATES PATENT AND TRADEMARK OFFICE
CERTIFICATE OF CORRECTION

PATENT NO.        : 7,115,786 B2
APPLICATION NO.  : 10/503498
DATED            : October 3, 2006
INVENTOR(S)      : Frederick Khachik It is certified that error appears in the above-identified patent and that said Letters Patent is hereby corrected as shown below:

In column 5, line 3 replace "Autein" with --lutein--.

In column 6, line 6 replace "A" with --a--.

In column 9, lines 54-55 make this line the subtitle of the next paragraph.

In column 14, lines 62 and 65, replace "confirmation" with --configuration--.

In column 15, line 64 replace "BPLC" with --HPLC--.

In column 16, line 4 replace "sulfuiric" with --sulfuric--.

In column 16, line 65 replace "aiihydrolutein" with --anhydrolutein--.

In column 17, line 4 replace "Sulfuiric" with --Sulfuric--.

Signed and Sealed this

Eighteenth Day of September, 2007

JON W. DUDAS
*Director of the United States Patent and Trademark Office*